United States Patent
Sirard et al.

(10) Patent No.: US 10,426,816 B2
(45) Date of Patent: Oct. 1, 2019

(54) METHODS AND PHARMACEUTICAL COMPOSITIONS FOR THE TREATMENT OF RESPIRATORY TRACT INFECTIONS

(71) Applicants: Jean-Claude Sirard, Lille (FR); Jose A. Chabalgoity, Montevideo (UY)

(72) Inventors: Jean-Claude Sirard, Lille (FR); Jose A. Chabalgoity, Montevideo (UY)

(73) Assignees: Institut National de la Sante et de la Recherche Medicale (INSERM), Paris (FR); Institut Pasteur de Lille, Lille (FR)

( * ) Notice: Subject to any disclaimer, the term of this patent is extended or adjusted under 35 U.S.C. 154(b) by 621 days.

(21) Appl. No.: 14/185,077

(22) Filed: Feb. 20, 2014

(65) Prior Publication Data

US 2014/0206601 A1    Jul. 24, 2014

Related U.S. Application Data

(63) Continuation of application No. 13/806,796, filed as application No. PCT/IB2010/001911 on Jun. 25, 2010, now abandoned.

(51) Int. Cl.
    *A61K 38/16* (2006.01)
    *C12Q 1/18* (2006.01)

(52) U.S. Cl.
    CPC .............. *A61K 38/164* (2013.01); *C12Q 1/18* (2013.01); *Y02A 50/387* (2018.01); *Y02A 50/389* (2018.01); *Y02A 50/463* (2018.01); *Y02A 50/473* (2018.01); *Y02A 50/475* (2018.01); *Y02A 50/481* (2018.01)

(58) Field of Classification Search
    USPC ........................................................ 514/2.6
    See application file for complete search history.

(56) References Cited

U.S. PATENT DOCUMENTS

2006/0257415 A1* 11/2006 Sirard et al. ............... 424/184.1
2009/0297552 A1* 12/2009 Aderem et al. ............ 424/192.1

FOREIGN PATENT DOCUMENTS

WO    2009/156405 A1    12/2009

OTHER PUBLICATIONS

CDC-Pneumococcal diseases (accessed Feb. 8, 2016).*
Yu et al., "Flagellin Stimulates Protective Lung Mucosal Immunity: Role of Cathelicidin-Related Antimicrobial Peptide", Journal of Immunology, Jun. 21, 2010, pp. 1142-1149, vol. 185, No. 2, Baltimore, MD.
Smith et al., "Toll-like receptor 5 recognizes a conserved site on flagellin required for protofilament formation and bacterial motility", Naturew Immunology, Dec. 1, 2003, pp. 1247-1253, vol. 4, No. 12, Nature Publishing, GB.
Nempont et al.; "Deletion of Flagellin's Hypervariable Region Abrogates Antibody-Mediated Neutralization and Systemic Activation of TLRS-Dependent Immunity"; Journal of Immunology, 2008, 181, pp. 2036-2043.
Accession No. AAL20871.1, Accessed Dec. 3, 2013.
Burdelya et al.; "An Agonist of Toll-Like Receptor 5 Has Radioprotective Activity in Mouse and Primate Models"; Science, vol. 320, Apr. 11, 2008, pp. 226-230.
"Therapeutic Intranasal Drug Delivery" (Accessed Nov. 21, 2013).

* cited by examiner

*Primary Examiner* — James H Alstrum-Acevedo
*Assistant Examiner* — Tara L Martinez
(74) *Attorney, Agent, or Firm* — W & C IP (57) ABSTRACT

The present invention relates to methods and pharmaceutical compositions for the treatment of respiratory tract infections. More particularly, the present invention relates to a TLR5 agonist for use in a method for treating a respiratory tract infection.

16 Claims, 2 Drawing Sheets

Specification includes a Sequence Listing.

METHODS AND PHARMACEUTICAL COMPOSITIONS FOR THE TREATMENT OF RESPIRATORY TRACT INFECTIONS

This application is a continuation of U.S. Ser. No. 13/806,796 filed Feb. 27, 2013, which itself was a national stage filing under Rule 371 of PCT/IB2010/001911 filed Jun. 25, 2010.

FIELD OF THE INVENTION

The present invention relates to methods and pharmaceutical compositions for the treatment of respiratory tract infections. More particularly, the present invention relates to a TLR5 agonist for use in a method for treating a respiratory tract infection.

BACKGROUND OF THE INVENTION

Respiratory tract infections are common infections of the upper respiratory tract (e.g., nose, ears, sinuses, and throat) and lower respiratory tract (e.g., trachea, bronchial tubes, and lungs). Symptoms of upper respiratory tract infection include runny or stuffy nose, irritability, restlessness, poor appetite, decreased activity level, coughing, and fever.

Viral respiratory tract infections cause and/or are associated with sore throats, colds, croup, and the flu. Examples of viruses that cause upper and lower respiratory tract infections include rhinoviruses and influenza viruses A and B.

Common respiratory bacterial infections cause and/or associated with, for example, whooping cough and strep throat. An example of a bacterium that causes upper and lower respiratory tract infections is *Streptococcus pneumoniae*, *Streptococcus pneumoniae* (pneumococcus) causes respiratory tract infections among infants and the elderly worldwide. Capsular polysaccharide is the main virulence factor, and its composition defines 91 serotypes of pneumococcus. Certain serotypes colonize asymptomatically the human nasopharynx representing a reservoir for inter-individual transmission of the bacteria. In some individuals colonization may progress to pneumococcal pneumonia and invasive disease. In contrast, serotypes like serotype 1 are rarely associated with colonization but cause invasive infections.

Current therapies for respiratory tract infections involve the administration of anti-viral agents, anti-bacterial, and antifungal agents for the treatment, prevention, or amelioration of viral, bacterial, and fungal respiratory tract infections, respectively. Unfortunately, in regard to certain infections, there are no therapies available, infections have been proven to be refractory to therapies, or the occurrence of side effects outweighs the benefits of the administration of a therapy to a subject. The use of anti-bacterial agents for treatment of bacterial respiratory tract infections may also produce side effects or result in resistant bacterial strains. The administration of antifungal agents may cause renal failure or bone marrow dysfunction and may not be effective against fungal infection in subjects with suppressed immune systems. Additionally, the infection causing microorganism (e.g., virus, bacterium, or fungus) may be resistant or develop resistance to the administered therapeutic agent or combination of therapeutic agents. In fact, microorganisms that develop resistance to administered therapeutic agents often develop pleiotropic drug or multidrug resistance, that is, resistance to therapeutic agents that act by mechanisms different from the mechanisms of the administered agents. Thus, as a result of drug resistance, many infections prove refractory to a wide array of standard treatment protocols.

Therefore, new therapies for the treatment, prevention, management, and/or amelioration of respiratory tract infections and symptoms thereof are needed.

Activation of innate defences is essential to control pneumococcal infection. Toll-like receptor 2 (TLR2), TLR4 and TLR9 as well as the adaptor MyD88 participate in the early detection and clearance of pneumococcus in the lungs. The cytosolic receptors nucleotide-binding oligomerization domain (Nod) containing Nod1 and Nod2, have also been involved in the recognition of pneumococci. TLR signaling activates mucosal innate responses that culminate with the recruitment of phagocytes like polymorphonuclear neutrophils (PMN) and macrophages and the production of microbicidal agents. This process triggers rapid eradication of the pathogen by phagocytosis as well as extracellular killing. In MyD88-deficient animals *S. pneumoniae* is unable to intrinsically trigger any PMN recruitment into airways and animals have increased susceptibility to pneumonia. The contribution of TLR signaling in humans has been highlighted by a recent study showing that some MyD88 polymorphisms are associated with increased susceptibility to pneumococcal infection.

Modulating immunity by the activity of innate receptors is an emerging concept to elicit protective responses against infections. The rationale is to promote innate responses that greatly exceed in magnitude, quality and dynamic the innate response triggered by the pathogen itself. The effectiveness of TLR agonists for therapeutic treatment of infectious diseases has been demonstrated in several animal models, including models of respiratory tract infections (Brown, K. L., C. Cosseau, J. L. Gardy and R. E. Hancock 2007. Complexities of targeting innate immunity to treat infection. Trends Immunol 28:260-266; Lembo, A., M. Pelletier, R. Iyer, M. Timko, J. C. Dudda, T. E. West, C. B. Wilson, A. M. Hajjar, and S. J. Skerrett. 2008. Administration of a synthetic TLR4 agonist protects mice from pneumonic tularemia. J Immunol 180:7574-7581; Romagne, F. 2007. Current and future drugs targeting one class of innate immunity receptors: the Toll-like receptors. Drug Discov Today 12:80-87). TLR5 senses bacterial flagellins that are the main constituent of flagella. Various cells of the pulmonary tract including the epithelial cells express TLR5 but the modulation of the TLR5 signalling pathway has not yet been investigated for the treatment of respiratory tract infections.

SUMMARY OF THE INVENTION

The present invention relates to methods and pharmaceutical compositions for the treatment of respiratory tract infections. More particularly, the present invention relates to a TLR5 agonist for use in a method for treating a respiratory tract infection.

DETAILED DESCRIPTION OF THE INVENTION

*Streptococcus pneumoniae* is a major cause of pneumonia in infants and the elderly. Innate defenses are essential to control pneumococcal infections and deficient responses can trigger disease in susceptible individuals. Here, the inventors showed that flagellin can locally activate innate immunity and thereby increase the resistance to acute pneumonia. Flagellin mucosal treatment improved *S. pneumoniae* clearance in the lungs and promoted increased survival to infection. In addition, lung architecture was fully restored after the treatment of infected mice, indicating that flagellin allows the re-establishment of steady state conditions. Using a flagellin mutant that is unable to signal through TLR5, they established that TLR5 signaling is essential for protection. In the respiratory tract, flagellin induced neutrophil infiltration into airways and upregulated the expression of genes coding for IL-6, TNF-α, CXCL1, CXCL2 and CCL20. Using depleting antibodies, they demonstrated that neutrophils are major effectors for protection. Further, they found that B and T cell-deficient SCID mice clear *S. pneumoniae* challenge to the same extent than immunocompetent animals suggesting that these cell populations are not required for flagellin-induced protection. In conclusion, the results emphasize that mucosal stimulation of innate immunity by a TLR not naturally engaged by *S. pneumoniae* can increase the potency to cure pneumococcal pneumonia. Moreover without whisking to be bound by any particular theory, the inventors believe that mucosal stimulation of innate immunity by TLR5 also represents a relevant way for the treatment of respiratory tract infections. For instance, microbial products like non-typeable *Haemophilus influenzae* lysates that are known to stimulate innate immunity by respiratory route are able to protect against various respiratory infections (Evans S E, Scott B L, Clement C G, Larson D T, Kontoyiannis D, Lewis R E, Lasala P R, Pawlik J, Peterson J W, Chopra A K, Klimpel G, Bowden G, Höök M, Xu Y, Tuvim M J, Dickey B F. Stimulated innate resistance of lung epithelium protects mice broadly against bacteria and fungi. Am J Respir Cell Mol Biol. 2010; 42:40-50), including *S. pneumoniae* infections (Clement C G, Evans S E, Evans C M, Hawke D, Kobayashi R, Reynolds P R, Moghaddam S J, Scott B L, Melicoff E, Adachi R, Dickey B F, Tuvim M J. Stimulation of lung innate immunity protects against lethal pneumococcal pneumonia in mice. Am J Respir Crit Care Med. 2008; 177:1322-30). Such respiratory infections include diseases that are induced by bacteria, viruses and fungi.

Therefore, the present invention relates to a TLR5 agonist for use in a method for treating a respiratory tract infection.

The term "respiratory tract infection" has its general meaning in the art and is intended to designated infections of the upper respiratory tract (e.g., nose, ears, sinuses, and throat) and lower respiratory tract (e.g., trachea, bronchial tubes, and lungs) induced by a live microorganism.

Examples of viruses which cause viral infections include, but are not limited to, retroviruses (e.g., human T-cell lymphotrophic virus (HTLV) types I and II and human immunodeficiency virus (HIV)), herpes viruses (e.g., herpes simplex virus (HSV) types I and Epstein-Barr virus, HHV6-HHV8, and cytomegalovirus), arenavirues (e.g., lassa fever virus), paramyxoviruses (e.g., morbillivirus virus, human respiratory syncytial virus, mumps, hMPV, and pneumovirus), adenoviruses, bunyaviruses (e.g., hantavirus), comaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C and PIV), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus).

Examples of bacteria which cause bacterial respiratory tract infections include, but not limited to, the Aquaspirillum family, Azospirillum family, Azotobacteraceae family, Bacteroidaceae family, Bartonella species, Bdellovibrio family, *Campylobacter* species, *Chlamydia* species (e.g., *Chlamydia pneumoniae*), *Clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter Family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum Family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus Fasciae*, and *Streptococcus pneumoniae*), Vampirovibr Helicobacter Family, and Vampirovibrio family.

Examples of fungi which cause fungal infections include, but not limited to, *Absidia* species (e.g., *Absidia corymbifera* and *Absidia ramosa*), *Aspergillus* species, (e.g., *Aspergillus fiavus, Aspergillus fumigatus, Aspergillus nidulans, Aspergillus niger*, and *Aspergillus terreus*), *Blastomyces dermatitidis, Candida* species (e.g., *Candida albicans, Candida glabrala, Candida kerr, Candida krusei, Candida parapsilosis, Candida pseudotropicalis, Candida quillermondii, Candida rugosa, Candida stellatoidea*, and *Candida tropicalis*), *Coccidioides immitis, Conidiobolus* species, *Cryptococcus neoforms, Cunninghamella* species, *Histoplasma capsulatum, Mucorpusillus, Paracoccidioides brasiliensis, Pseudallescheria boydii, Pneumocystis carinii, Rhizopus* species (e.g., *Rhizopus arrhizus, Rhizopus oryzae*, and *Rhizopus* Microspores), *Saccharomyces* species, and *Sporothrix schenckii*.

In a particular embodiment, the respiratory tract infection according to the invention is a bacterial respiratory tract infection, more particularly a respiratory tract infection that results from bacteria that do not have flagella. Typically, bacteria that do not have flagella and cause respiratory tract infection include *Streptococcus pneumoniae, Haemophilus influenzae Moraxella catarrhalis*, or *Mycoplasma pneumoniae*. Even more preferably, the respiratory tract infection according to the invention is a pneumococcal infection.

As used herein the term "toll-like receptor 5" or "TLR5" has its general meaning in the art and is intended to mean a toll-like receptor 5 of any species, but preferably a human toll-like receptor 5. Upon activation, a TLR5 induces a cellular response by transducing an intracellular signal that is propagated through a series of signaling molecules from the cell surface to the nucleus. Typically, the intracellular domain of TLR5 recruits the adaptor protein, MyD88, which recruits the serine/threonine kinases IRAK (IRAK-1 and IRAK-4). IRAKs form a complex with TRAF6, which then interacts with various molecules that participate in transducing the TLR signal. These molecules and other TLR5 signal transduction pathway components stimulate the activity of transcription factors, such as fos, jun and NF-kB, and the corresponding induction of gene products of fos-, jun- and NF-kB-regulated genes, such as, for example, IL-6, TNF-α, CXCL1, CXCL2 and CCL20.

As used herein, the term "TLR5 agonist" refers to a compound (natural or not) that selectively activates or increases normal signal transduction through TLR5. A TLR5 agonist can activate or increase normal signal transduction through TLR5 indirectly, for example, by modifying or altering the native conformation of TLR5 or a TLR5 ligand. The activities of signalling molecules that mediate the TLR5 signal, as well as molecules produced as a result of TLR5 activation are TLR5 activities that can be observed or measured. Therefore, a TLR5 activity includes recruitment of intracellular signaling molecules, as well as downstream events resulting from TLR5 activation, such as transcription factor activation and production of immunomodulatory molecules. A TLR5 cellular response mediates an innate immune system response in a subject because cytokines released by TLR5-expressing cells regulate other immune system cells to promote an immune response in a subject. Therefore, as used herein the term "TLR5-mediated response" is intended to mean the ability of TLR5 agonist to induce a TLR5-mediated cellular response. Exemplary TLR5-mediated cellular responses include activation of transcription factors such as fos, jun and NF-kB, production of cytokines and chemokines such as IL-6, TNF-α, CXCL1, CXCL2 and CCL20, and the stimulation of an immune response in a subject.

In one embodiment, the TLR5 agonist according to the invention is a low molecular weight agonist, e.g. a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Alternatively, the TLR5 agonist according to the invention may consist in an antibody (the term including "antibody fragment"). In particular, the TLR5 agonist may consist in an antibody directed against TLR5, in such a way that said antibody activates the receptor.

Antibodies can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique. Alternatively, techniques described for the production of single chain antibodies (see, e.g., U.S. Pat. No. 4,946,778) can be adapted to produce anti-TLR5 single chain antibodies.

The TLR5 agonist useful in practicing the present invention also include anti-TLR5 antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to TLR5.

Humanized antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies as above described, the skilled man in the art can easily select those that are TLR5 agonists.

In another embodiment the TLR5 agonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods.

Then after raising aptamers directed against TLR5 as above described, the skilled man in the art can easily select those that are TLR5 agonists.

In another particular embodiment, the TLR5 agonist according to the invention is a polypeptide, and more particularly a flagellin polypeptide.

As used herein, the term "flagellin" is intended to mean the flagellin contained in a variety of Gram-positive or Gram-negative bacterial species. Non-limiting sources of flagellins include but are not limited to Escherichia, e.g., E. coli, Enterobacter, Erwinia, Klebsiella, Proteus, Salmonella, e.g., Salmonella enterica serovar Typhimurium, Serratia, e.g., Serratia marceseans, and Shigella, as well as Bacilli such as B. subtilis and B. licheniformis, Pseudomonas such as P. aeruginosa, and Streptomyces. These examples are illustrative rather than limiting. The amino acid sequences and nucleotide sequences of flagellins are publically available in the NCBI Genbank, see for example Accession Nos. AAL20871, NP_310689, BAB58984, AAO85383, AAA27090, NP_461698, AAK58560, YP_001217666, YP_002151351, YP_001250079, AAA99807, CAL35450, AAN74969, and BAC44986. The flagellin sequences from these and other species are intended to be encompassed by the term flagellin as used herein. Therefore, the sequence differences between species are included within the meaning of the term.

The term "flagellin polypeptide" is intended to a flagellin or a fragment thereof that retains the ability to bind and activate TLR5. Typically, the flagellin polypeptide according to the invention comprises the domains of flagellin involved in TLR5 signaling. The term "domain of flagellin" includes naturally occurring domain of flagellin and function conservative variants thereof. "Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared. The domains of flagellin that are involved in TLR5 signaling are well known in the art, see for example Smith et al. (2003) Nat. Immunol. 4: 1247-1253 (e.g., amino acids 78-129, 135-173 and 394-444 of *S. typhimurium* flagellin or homologs or modified forms thereof).

Examples of flagellin polypeptides include but are not limited to those described in U.S. Pat. Nos. 6,585,980; 6,130,082; 5,888,810; 5,618,533; and 4,886,748; U.S. Patent Publication No. US 2003/0044429 A1; and in the International Patent Application Publications no WO 2008097016 and WO 2009156405 which are incorporated by reference.

An exemplary *E. coli* O157:H7 flagellin is SEQD ID NO:1. An exemplary *S. typhimurium* flagellin is SEQ ID NO:2 or SEQ ID NO:3. Amino acid sequences at least about 90%, at least about 95%, at least about 97%, at least about 98% or at least about 99% identical to SEQ ID NO: 1 SEQ ID NO:2 or SEQ ID NO:3 can be used as flagellin polypeptides according to the invention.

In another particular embodiment, the present encompasses use of the flagellin recombinant proteins described in the International Patent Application no WO 2009156405 which is incorporated by reference in its entirely. Accordingly, a flagellin polypeptide of the invention may comprise: a) a N-terminal peptide having at least 90% amino acid identity with the amino acid sequence starting from the amino acid residue located at position 1 of SEQ ID NO:3 and ending at an amino acid residue selected from the group consisting of any one of the amino acid residues located at positions 99 to 173 of SEQ ID NO:3; and b) a C-terminal peptide having at least 90% amino acid identity with the amino acid sequence starting at an amino acid residue selected from the group consisting of any one of the amino acid residues located at positions 401 to 406 of SEQ ID NO:3 and ending at the amino acid residue located at position 494 of SEQ ID NO:3, wherein: the said N-terminal peptide is directly linked to the said C-terminal peptide, or the said N-terminal peptide and the said C-terminal peptide are indirectly linked, one to the other, through a spacer chain. In another particular embodiment, said N-terminal peptide is selected from the group consisting of the amino acid sequences 1-99, 1-137, 1-160 and 1-173 of SEQ ID NO:3. In another embodiment, said C-terminal peptide is selected from the group consisting of the amino acid sequences 401-494 and 406-494 of SEQ ID NO:3. In another embodiment, said N-terminal and C-terminal peptides consist of the amino acid sequences 1-173 and 401-494 of SEQ ID NO:3, respectively. In another embodiment, said N-terminal and C-terminal peptides consist of the amino acid sequences 1-160 and 406-494 of SEQ ID NO:3, respectively. In another embodiment, said N-terminal and C-terminal peptides consist of the amino acid sequences 1-137 and 406-494 of SEQ ID NO:3, respectively. In another embodiment, said N-terminal peptide and the said C-terminal peptide are indirectly linked, one to the other, through an intermediate spacer chain consisting of a NH2-Gly-Ala-Ala-Gly-COOH (SEQ ID NO:4) peptide sequence. In another embodiment, the asparagine amino acid residue located at position 488 of SEQ ID NO:3 is replaced by a serine. In another embodiment, the flagellin polypeptide as above described comprises an additional methionine residue at the N-terminal end.

The flagellin polypeptide according to the invention may be recombinantly produced by recombinant cells that have been transfected with a nucleic acid that encodes its amino acid sequence and allows its effective production within the transfected cells.

The nucleic acid sequence encoding the flagellin polypeptide of the invention, may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art.

Vector components generally include, but are not limited to, one or more of a signal sequence if the sequence is to be secreted, an origin of replication, one or more marker genes, an enhancer element, a promoter, and a transcription termination sequence. Construction of suitable vectors containing one or more of these components employs standard ligation techniques that are known to the skilled artisan.

The flagellin polypeptides of the invention may be produced recombinantly not only directly, but also as a fusion polypeptide with a heterologous polypeptide, which may be a signal sequence or other polypeptide having a specific cleavage site at the N-terminus of the mature protein or peptide. In general, the signal sequence may be a component of the vector, or it may be a part of the DNA encoding the polypeptide of interest that is inserted into the vector. The signal sequence may be a prokaryotic signal sequence selected, for example, from the group of the alkaline phosphatase, penicillinase, Ipp, or heat-stable enterotoxin II leaders. For yeast secretion the signal sequence may be, e.g., the yeast invertase leader, alpha factor leader (including *Saccharomyces* and *Kluyveromyces* .alpha.-factor leaders, the latter described in U.S. Pat. No. 5,010,182), or acid phosphatase leader, the *C. albicans* glucoamylase leader, or the signal described in WO 90/13646. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2.mu. plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the nucleic acid encoding the flagellin polypeptide of the invention such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77: 4216 (1980). A suitable selection gene for use in yeast is the trp 1 gene present in the yeast plasmid YRp7. Stinchcomb et al., Nature, 282: 39 (1979); Kingsman et al., Gene, 7: 141 (1979); Tschemper et al, Gene, 10: 157 (1980). The trp1 gene provides a selection marker for a mutant strain of yeast lacking the ability to grow in tryptophan, for example, ATCC No. 44076 or PEP4-1. Jones, Genetics, 85: 12 (1977).

Expression and cloning vectors usually contain a promoter operably linked to the nucleic acid sequence encoding the flagellin polypeptide to direct mRNA synthesis. Promoters recognized by a variety of potential host cells are well known. Promoters suitable for use with prokaryotic hosts include the beta-lactamase and lactose promoter systems (Chang et al., Nature, 275: 615 (1978); Goeddel et al., Nature, 281: 544 (1979)), alkaline phosphatase, a tryptophan (trp) promoter system (Goeddel, Nucleic Acids Res., 8:4057 (1980); EP 36,776), and hybrid promoters such as the tac promoter (deBoer et al., Proc. Natl. Acad. Sci. USA, 80: 21-25 (1983)). promoters for use in bacterial systems also will contain a Shine-Dalgarno (S. D.) sequence operably linked to the DNA encoding the flagellin polypeptide of the invention.

Examples of suitable promoting sequences for use with yeast hosts include the promoters for 3-phosphoglycerate kinase (Hitzeman et al., J. Biol. Chem., 255: 2073 (1980)) or other glycolytic enzymes (Hess et al., J. Adv. Enzyme Reg., 7: 149 (1968); Holland, Biochemistry, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters that are inducible promoters having the additional advantage of transcription controlled by growth conditions are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Nucleic acid of interest transcription from vectors in mammalian host cells is controlled, for example, by promoters obtained from the genomes of viruses such as polyoma virus, fowl pox virus (UK 2,211,504 published 5 Jul. 1989), adenovirus (such as Adenovirus 2), bovine papilloma virus, avian sarcoma virus, cytomegalovirus, a retrovirus, hepatitis-B virus, and Simian Virus 40 (SV40); by heterologous mammalian promoters, e.g., the actin promoter or an immunoglobulin promoter; and by heat-shock promoters, provided such promoters are compatible with the host cell systems.

Transcription of a DNA encoding the flagellin polypeptide of the invention by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the sequence coding for polypeptides of interest, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the flagellin polypeptide of the invention.

Still other methods, vectors, and host cells suitable for adaptation to the synthesis of the flagellin polypeptide of the invention in recombinant vertebrate cell culture are described in Gething et al., Nature, 293: 620-625 (1981); Mantei et al., Nature, 281: 40-46 (1979); EP 1 17,060; and EP 1 17,058.

Selection and Transformation of Host Cells Host cells are transfected or transformed with expression or cloning vectors described herein for flagellin polypeptide production and cultured in conventional nutrient media modified as appropriate for inducing promoters, selecting transformants, or amplifying the genes encoding the desired sequences.

The culture conditions, such as media, temperature, pH, and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991).

Methods of transfection are known to the ordinarily skilled artisan, for example, CaPO4 treatment and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., J. Bact, 130: 946 (1977) and Hsiao et al., Proc. Natl. Acad. Sci. (USA), 76: 3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., Methods in Enzymology, 185: 527-537 (1990) and Mansour et al., Nature, 336: 348-352 (1988).

Suitable host cells for cloning or expressing the DNA in the vectors herein include prokaryote, yeast, or higher eukaryote cells.

Suitable prokaryotes include, but are not limited to, eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5772 (ATCC 53,635). Other suitable prokaryotic host cells include Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published 12 Apr. 1989), *Pseudomonas* such as *P. aeruginosa*, and *Streptomyces*. These examples are illustrative rather than limiting.

Strain SIN41 of *Salmonella typhimurium* (fliC fljB), is particularly interesting for the production of flagellin polypeptides of the invention, since these prokaryotic host cells do not secrete any flagellins (Proc Natl Acad Sci USA. 2001; 98:13722-7). However flagellins are secreted through specialized secretion system: the so called "Type III secretion system". Interestingly, strain SIN41 produces all components of the type III secretion system required for optimal flagellin secretion. Cloning sequence coding new flagellin peptides under fliC promoter enables secretion in large amounts of the flagellin polypeptides of interest in strain SIN41.

Strain W3110 is also interesting because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W31 10 strain 27C7 (ATCC 55,244), which has the complete genotype tonA ptr3 phoA E15 (argF-lac)169 degP ompT kan.sup.r; *E. coli* W31 10 strain 37D6, which has the complete genotype tona ptr3 phoA E15 (argF-lac)169 degP ompT rbs7 ilvG kan.sup.r; *E. coli* W31 10 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. The *E. coli* strains MG1655, MG1655 AfimA-H or MKS12, a fliD- and -f/m>A-/-/-deleted MG1655 strain are also interesting candidates for production of recombinant flagellins as secreted proteins (Nat Biotechnol. 2005; (4):475-81). Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors encoding the flagellin polypeptides according to the invention. *Saccharomyces cerevisiae* is a commonly used lower eukaryotic host microorganism.

Others include *Schizosaccharomyces pombe* (Beach and Nurse, Nature, 290: 140 [1981]; EP 139,383 published 2 May 1985); *Kluyveromyces* hosts (U.S. Pat. No. 4,943,529; Fleer et al., Bio/Technology, 9: 968-975 (1991)) such as, e.g., *K. lactic* (MW98-8C, CBS683, CBS4574; Louvencourt et al., J. Bacterid., 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402, 226); *Pichia pastoris* (EP 183,070; Sreekrishna et al., J. Basic Microbiol., 28: 265-278 [1988]); *Candida; Trichoderma reesia* (EP 244,234); *Neurospora crassa* (Case et al., Proc. Natl. Acad. Sci. USA, 76: 5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112: 284-289 [1983]; Tilbum et al., Gene, 26: 205-221 [1983]; Yelton et al., Proc. Natl. Acad. Sci. USA, 81: 1470-1474 [1984]) and *A. niger* (Kelly and Hynes, EMBO J., 4: 475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. Suitable host cells for the expression of nucleic acid encoding flagellin polypeptide of the invention are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen. Virol., 36: 59 (1977)); Chinese hamster ovary cells/-DHFR(CHO, Urlaub and Chasin, Proc. Natl. Acad. Sci. USA, 77:4216 (1980)); mouse Sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Flagellin polypeptide of the invention may be recovered from culture medium or from host cell lysates. If membrane-bound, it can be released from the membrane using a suitable detergent solution (e.g., TRITON-X™ 100) or by enzymatic cleavage.

Cells employed in expression of nucleic acid encoding the flagellin polypeptide of the invention can be disrupted by various physical or chemical means, such as freeze-thaw cycling, sonication, mechanical disruption, or cell-lysing agents. It may be desired to purify the polypeptide of interest from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; Protein A Sepharose columns to remove contaminants such as IgG; and metal chelating columns to bind epitope-tagged forms of the flagellin polypeptide of the invention.

Various methods of protein purification may be employed and such methods are known in the art and described, for example, in Deutscher, Methods in Enzymology, 182 (1990); Scopes, Protein Purification: Principles and Practice (Springer-Verlag: New York, 1982). The purification step(s)

selected will depend, for example, on the nature of the production process used and the particular flagellin polypeptide produced.

In a preferred embodiment, the flagellin polypeptide is purified from the supernatant of recombinant *S. Typhimurium* SIN41 (fliC fljB), as disclosed in Nempont et al. (Nempont, C. C., D.; Rumba, M.; Bompard, C.; Villeret, V.; Sirard, J. C. 2008. Deletion of flagellin's hypervariable region abrogates antibody-mediated neutralization and systemic activation of TLR5-dependent immunity. J Immunol 181:2036-2043). In particular, *Salmonella* were grown in Luria-Bertani (LB) broth for 6-18 hours at 37° C. with agitation. The supernatant was filtered and saturated with 60% ammonium sulfate (Sigma Aldrich, USA). The precipitated materials were recovered by centrifugation, solubilization in 2 OmM Tris/HCl pH 7.5 and then dialysis. The proteins were further purified by successive rounds of hydroxyapatite, anion exchange, and size exlusion chromatography (Bio-Rad Laboratories, USA; GE Healthcare, Sweden). Lastly, the proteins were depleted of lipopolysaccharide (LPS) using a polymyxin B column (Pierce, USA). Using the Limulus assay (Associates of Cape Cod Inc., USA), the residual LPS concentration was determined to be less than 30 pg LPS per µg recombinant flagellin.

In further embodiments, a flagellin polypeptide according to the invention may be purified by separation on an immunoaffinity chromatography substrate.

Said immunoaffinity chromatography substrate comprises anti-flagellin antibodies that have been immobilized thereon. By "anti-flagellin" antibodies, it is intended herein antibodies that bind to either a native flagellin or to a hypervariable region-deleted flagellin, including those encompassed by the present invention.

Preferably, the anti-flagellin antibodies consist of monoclonal antibodies, including mouse anti-flagellin antibodies.

In certain embodiments, a polypeptide of the invention may be synthesized through conventional techniques of chemical peptide synthesis.

For instance, the flagellin polypeptide sequence of the invention may be produced by direct peptide synthesis using solid-phase techniques.

In vitro protein synthesis may be performed using manual techniques or by automation. Automated synthesis may be accomplished, for instance, with an Applied Biosystems Peptide Synthesizer (Foster City, Calif.) using manufacturer's instructions.

Various portions of the polypeptide of interest may be chemically synthesized separately and combined using chemical or enzymatic methods to produce the full-length peptide of interest.

The present invention also relates to pharmaceutical compositions for use in a method for treating a respiratory tract infection comprising a TLR5 agonist according to the invention.

Typically, the TLR5 agonists according to the invention may be combined with pharmaceutically acceptable excipients, and optionally sustained-release matrices, such as biodegradable polymers, to form therapeutic compositions. "Pharmaceutically" or "pharmaceutically acceptable" refers to molecular entities and compositions that do not produce an adverse, allergic or other untoward reaction when administered to a mammal, especially a human. A pharmaceutically acceptable carrier or excipient refers to a non-toxic solid, semi-solid or liquid filler, diluent, encapsulating material or formulation auxiliary of any type.

The pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic to ease pain at the site of the injection.

Preferably, the pharmaceutical composition of the invention is administered topically (i.e. in the respiratory tract of the subject). Therefore, the compositions can be formulated in the form of an ointment, cream, transdermal patch, lotion, gel, spray, aerosol, solution, emulsion, or other form well-known to one of skill in the art. For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

The method of the invention may comprise pulmonary administration, e.g., by use of an inhaler or nebulizer, of a composition formulated with an aerosolizing agent. See, e.g., U.S. Pat. Nos. 6,019,968, 5,985, 320, 5,985,309, 5,934, 272, 5,874,064, 5,855,913, 5,290,540, and 4,880,078; and PCT Publication Nos. WO 92/19244, WO 97/32572, WO 97/44013, WO 98/31346, and WO 99/66903, each of which his incorporated herein by reference in their entirety. In a specific embodiment, the pharmaceutical composition of the invention is administered using Alkermes AIR™ pulmonary drug delivery technology (Alkermes, Inc., Cambridge, Mass.).

Accordingly, the invention provides a method of preventing, treating, managing, or ameliorating a respiratory tract infection or one or more symptoms thereof comprising administering a subject in need thereof with a therapeutically effective amount of a TLR5 agonist.

According to the invention, the term "subject" or "individual" to be treated is intended for a human or non-human mammal (such as a rodent (mouse, rat), a feline, a canine, or a primate) affected or likely to be affected with cancer. Preferably, the subject is a human.

The term "therapeutically effective amount" is meant for a sufficient amount of polypeptide or nucleic acid in order to treat cancer, at a reasonable benefit/risk ratio applicable to any medical treatment. It will be understood, however, that the total daily usage of the polypeptide and pharmaceutical compositions of the present invention will be decided by the attending physician within the scope of sound medical judgment. The specific therapeutically effective dose level for any particular subject will depend upon a variety of factors including the disorder being treated and the severity of the disorder; the activity of the polypeptide employed; the specific composition employed, the age, body weight, general health, sex and diet of the subject; the time of administration, route of administration, the duration of the treatment; the drugs used in combination or coincidental with the specific polypeptide employed; and like factors well known in the medical arts.

The invention will be further illustrated by the following figures and examples. However, these examples and figures should not be interpreted in any way as limiting the scope of the present invention.

FIGURES

FIG. 1: Flagellin protects BALB/c mice against a lethal respiratory challenge with $S.$ $pneumoniae$: BALB/c mice (n=8) were infected i.n. with $4 \times 10^5$ CFU of $S.$ $pneumoniae$ (Sp) serotype 1 in saline alone (black square), or supplemented with 1 µg Flagellin (FliC, black circle) or supplemented with 1 µg trypsin-digested flagellin (FliC/T, open circle). (A) Mice survival was daily monitored. Survival for FliC-treated group was statistically significant compared to saline group or FliC/T-treated group. Results are representative of 1 out of 3 experiments. (B) Mice were sacrificed 24 h after challenge and the number of colony forming units (CFU) was determined in the lungs. Significant differences between groups are marked with asterisk; $P<0.05$ (*). Results are representative of 1 out of 3 experiments. Error bars represent the mean±Standard error of the mean (SEM).

EXAMPLE

Material & Methods
Bacterial Preparation:
$Streptococcus$ $pneumoniae$ serotype 1 (clinical isolate E1586) was obtained from the National Reference Laboratory—Ministry of Health, Uruguay (39). Working stocks were prepared as follows. Todd Hewitt Yeast Broth (THYB) (Sigma-Aldrich, St. Louis, Mo., USA) was inoculated with fresh colonies of $S.$ $pneumoniae$ grown in blood-agar plates, and incubated at 37° C. until the culture reached $OD_{600\ nm}$ of 0.7-0.9 units. Cultures were stored at −80° C. in THYB+ glycerol 12% (v/v) up to 3 months. For mouse infection, working stocks were thawed and washed with sterile physiological saline solution (saline) and diluted to the appropriate concentration. Number of bacteria in stocks was confirmed by plating serial dilutions onto blood agar plates.

Proteins:
Native flagellin (FliC) from $Salmonella$ $enterica$ Serovar Typhimurium SIN22, or recombinant flagellins (FliC$_{\Delta 174\text{-}400}$ and FliC$_{\Delta 174\text{-}400/89\text{-}96*}$) were prepared as previously described (27). FliC$_{\Delta 174\text{-}400/89\text{-}96*}$ carries aminoacids substitution (89-96) that prevents TLR5 signaling. All proteins contained low LPS amount (less than 30 pg LPS per µs, determined with the Limulus assay). In some experiments, trypsin-hydrolyzed FliC (FliC/T) was used as a control. Native FliC was heated for 5 minutes at 65° C. before use to ensure that proteins are mostly monomers. Unless specified, 1 µg FliC, FliC/T, FliC$_{\Delta 174\text{-}400}$ or FliC$_{\Delta 174\text{-}400/89\text{-}96*}$ was co-administered i.n. with the $S.$ $pneumoniae$ suspension. To exclude any direct effect of flagellin on bacterial viability, viable counts were determined prior and after incubation of $S.$ $pneumoniae$ with the same concentration of flagellin used for the in vivo assay. There were no significant differences in the number of bacteria recovered after incubation with flagellin compared to control condition.

Animal Infections:
Female BALB/c, C57BL/6J and outbred NMRI strain (6-8 weeks old) were obtained from the National Division of Veterinary Laboratories (Uruguay) or Janvier laboratories (France). Female SCID mice (C.B-17 SCID) were obtained from Institut Pasteur de Lille breeding facilities. These mice are characterized by the lack of B and T lymphocytes and agammaglobulinaemia. Animals were maintained in individually ventilated cages and handled in a vertical laminar flow cabinet (class II A2, ESCO, Pennsylvania-USA) for infection. All experiments complied with current national and institutional regulations and ethical guidelines (CHEA—Universidad de la República, Uruguay and #A59107—Institut Pasteur de Lille). Mice were anaesthetized by intraperitoneal (i.p.) injection of 2.2 mg Ketamine (Richmond-Vet Pharma, Bs. As.—Argentina) plus 0.11 mg Xylazine (Portinco, Montevideo—Uruguay) in a total volume of 200 µl or by inhalation of Isoflurane (Belamont, SAS, France) using an anaesthesia non-rebreathing system (DRE-Compact 150, DRE Veterinary, Louisville—US). Bacteria and flagellins were administrated onto mice's nostrils in 20 to 50 µl of saline. Mice survival was recorded daily.

For depletion of granulocytes, 100 µg of anti-Gr-1 (RB6-8C5) or isotype control (HB152) were administered i.p. 24 h before i.n. challenge with $S.$ $pneumoniae$ (24). The anti-Gr1 injection was found to deplete 96.8±1.2% PMNs in Bronchoalveolar Lavages (BAL) after flagellin intranasal treatment.

Determination of Bacterial Load in Lungs and Spleen:
Lungs and spleen were collected at selected time points after intranasal challenge and homogenized with an Ultra-Turrax homogenizer (IKA-Werke, Staufen-Germany). Viable counts were determined by plating serial dilutions onto blood-agar plates.

Quantitative RT-PCR (qRT-PCR):
Lungs were homogenized in Trizol reagent (Invitrogen, California-USA) with UltraTurrax homogenizer and stored at −80° C. RNA extraction was performed according manufacturer's instructions. Prior to cDNA synthesis, 1 µg total RNA was treated with DNAse-I (Invitrogen), and first strand complementary DNA (cDNA) synthesis was carried out using random primers (Invitrogen) and M-MLV reverse transcriptase (Invitrogen). Real-time PCR was performed using QuantiTect® SYBR® Green PCR Kit (Qiagen, Hilden-Germany) in a Rotor-Gene 6000 (Corbett, Sydney-Australia) according to the following protocol: 15 min at 95° C. followed by 40 cycles at 95° C. for 15 sec and 60° C. for 1 min. Primers were used in a final concentration of 0.9 µM. The expression of the gene of interest was normalized using β-actin as housekeeping gene. Results are presented as fold increase in mRNA levels compared to saline-treated group.

Determination of PMN Infiltration into the Airways and Lungs:

For bronchoalveolar lavages (BAL) sampling trachea was cannulated and 1 ml of PBS+1 mM EDTA was instilled six times and recovered by gentle aspiration; this process was repeated twice. Cells were suspended in FACS-EDTA buffer (PBS, 0.1% azide, 1% bovine serum albumin from Sigma-Aldrich plus 5 mM EDTA). Lung cells were isolated after collagenase/DNAse treatment as previously described (34) and filtered through a 40 µm cell strainer. Immune cells were separated in a two-layered Percoll (Sigma-Aldrich) gradient. Briefly, cells were suspended in 35% isotonic Percoll solution, carefully placed on top of a 70% isotonic Percoll solution and centrifuged 30 min at 2600 g and RT without brake. Top ring of cells corresponding mostly to epithelial cells was discarded and immune cells were recovered from the ring of cells closest to the 70% Percoll layer. Cells were filtered using a 100 µm cell strainer washed and stained for FACS analysis. Neutrophils were identified by FSC-SSC and positive staining for PE- or Alexa Fluor 647-conjugated anti-Ly-6G (clone 1A8), PerCP-Cy5.5-conjugated anti-Ly-6C (Clone HK1.4) or PE-conjugated anti-CD11b (clone M1/70) from BD Biosciences or BioLegend, California-USA. After fixation with PFA 4%, flow cytometry data acquisition was performed on a FACS Calibur Cytometer with CellQuest 3.3 software (BD Biosciences).

Histological Analysis:

Lungs were fixed in 4% formalin (Sigma-Aldrich) for 24 h and then embedded in paraffin. Lung blocks were sectioned at 5 µm using a Leica microtome (Leica Microsystems, Wetzlar-Germany) and adhered to silanized slides. Hematoxylin/eosin stained sections were analyzed using a Nikon Eclipse 80i microscope and a Nikon DS-Ri1 digital camera and processed using NIS-Elements BR 3.0 software by Laboratory Imaging.

Statistical Analysis:

Log-rank (Mantel-Cox) test was performed for analysis of survival curves. For comparison between two groups Mann-Whitney test was performed. P values<0.05 were considered significant in all cases. Statistical analysis was carried out using GraphPad Prism program (GraphPad Software, San Diego Calif. USA).

Results

Intranasal Delivery of Flagellin Protects Mice Against a Lethal Challenge with S. pneumoniae:

We first determined the minimal dose of S. pneumoniae that causes 100% mortality in BALB/c mice upon intranasal (i.n.) administration. Animals were infected with increasing doses of a clinical isolate of S. pneumoniae serotype 1 and survival was assessed daily. We defined $4 \times 10^5$ CFU as the minimal lethal dose (MLD) that kills all animals within 72 to 120 h.

Figure 1A:
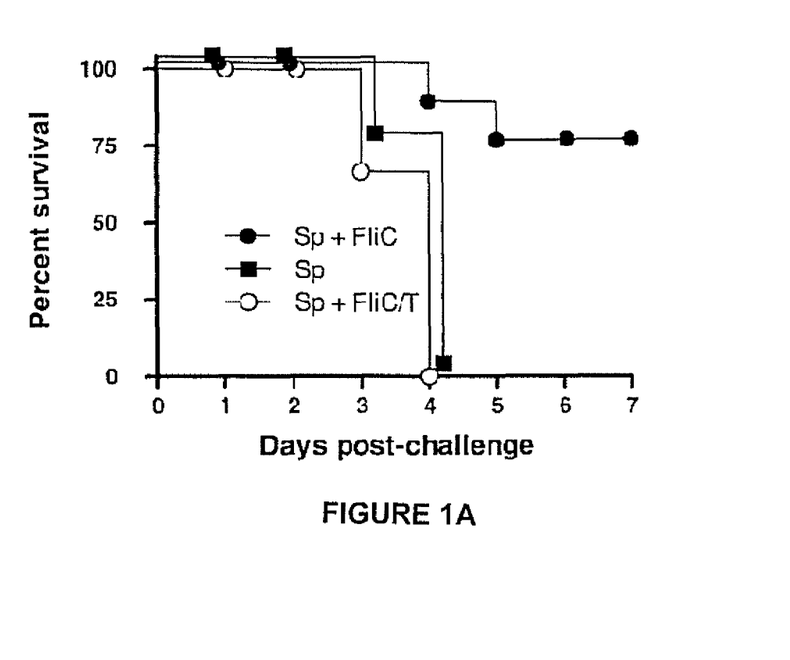
Figure 1B:
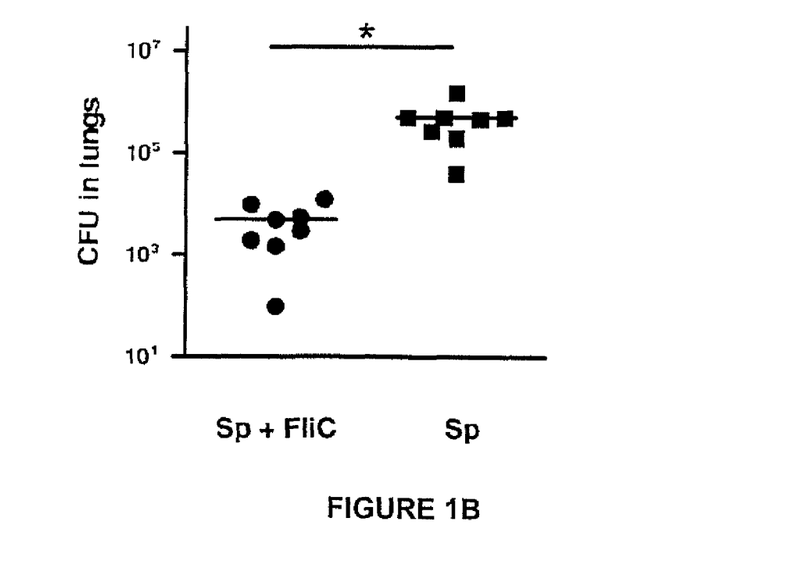

The capacity of flagellin to control pneumococcal pneumonia was then assessed by comparing the survival of mice challenged intranasally with S. pneumoniae to mice instilled with flagellin (FliC) and S. pneumoniae. As a control, mice were also challenged with S. pneumoniae and flagellin previously hydrolyzed with trypsin (FliC/T). As shown in FIG. 1A, FliC-treated mice had a survival rate of 75%, while untreated or FliC/T-treated animals died within 3 to 4 days after challenge. The protection induced by flagellin ranged from 75 to 100% between different independent experiments. Co-administration of flagellin with S. pneumoniae resulted within 24 h in an 80-fold reduction of bacterial counts in the lungs as compared with animals that received S. pneumoniae alone (FIG. 1B). We also evaluated whether flagellin could exert a protective response against pneumococcal infection when administered before and after the infection. All animals receiving flagellin intranasally 12 to 24 h before pneumococcal challenge survived, while all control mice died by day 4. Moreover, 100% protection was also achieved when flagellin was administered 24 h after the challenge. Therefore, flagellin shows prophylactic and therapeutic effects in pneumococcal pneumonia.

The capacity of flagellin to induce protection was also assessed in C57BL/6 and the outbred strain NMRI. The MLD of S. pneumoniae serotype 1 was found to be $2 \times 10^6$ CFU for both strains, and flagellin-mediated protection was evaluated with 5×MLD. Administration of flagellin 12 h before bacterial challenge induced 80% protection in C57BL/6 mice; similarly, 100% protection was achieved in NMRI animals when flagellin was administered 32 h to 6 h before challenge. Flagellin was also protective when co-administered with S. pneumoniae in C57BL/6 and NMRI strains, although to a lower extent (40%). Altogether, these results show that flagellin treatment is protective in different mouse strains.

Figure 2:
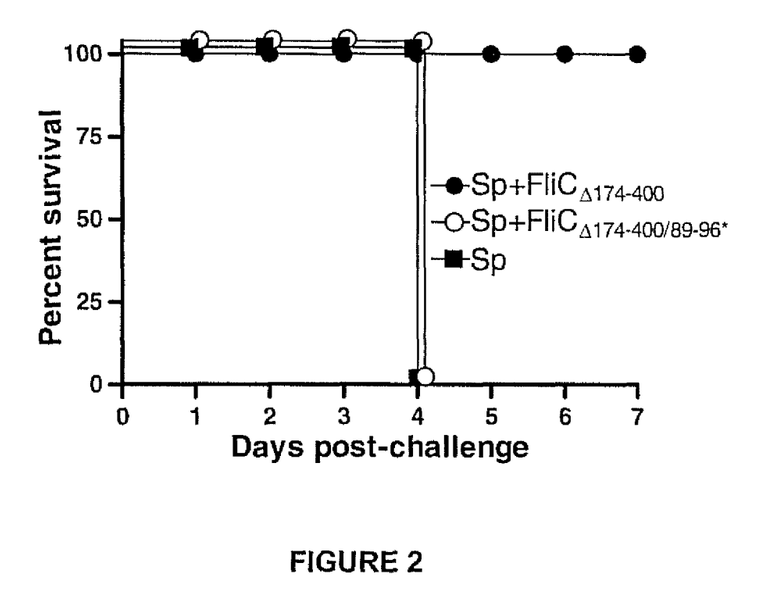
FIG. 2: TLR5 signaling is required for flagellin-mediated protection against $S.$ $pneumoniae$ infection: BALB/c mice (n=8) were infected i.n. with $4 \times 10^5$ CFU of $S.$ $pneumoniae$ (Sp) serotype 1 in saline alone (black square), or supplemented with 1 µg FliC Δ174-400 (black circle) or with 1 µg FliC$_{\Delta 174\text{-}400/89\text{-}96*}$ lacking TLR5-signaling motif (open circle). Mice survival was recorded daily. Survival for FliC Δ174-400-treated group was statistically significant compared to untreated group or FliC$_{\Delta 174\text{-}400/89\text{-}96*}$-treated group ($P<0.05$). Results are representative of 1 out of 2 experiments.

We next addressed whether TLR5 signaling is necessary for the protection elicited by flagellin treatment. For this, we used the recombinant flagellins $FliC_{\Delta 174-400}$ and $FliC_{\Delta 174-400/89-96*}$ (27). $FliC_{\Delta 174-400}$ has the same capacity to promote mucosal TLR5 signaling as native flagellin, whereas $FliC_{\Delta 174-400/89-96*}$ carries mutations that prevents TLR5 signaling. Whereas all mice that received $FliC_{\Delta 174-400}$ and S. pneumoniae survived the challenge, none of those receiving the mutant $FliC_{\Delta 174-400/89-96*}$ did so (FIG. 2). These results strongly suggest that TLR5 signaling is required for protection.

Flagellin Treatment Promotes Pro-Inflammatory Gene Expression and Exacerbates Transient Cellular Infiltration into the Lungs During Pneumococcal Pneumonia:

We then analyzed whether flagellin treatment modify the lung transcriptional response to pneumococcal infection. Mice were challenged with S. pneumoniae or with S. pneumoniae plus flagellin as before. Another group received flagellin alone as control. Twenty four hours after treatment and infection, lungs were harvested to analyze the expression of selected genes by qRT-PCR. Administration of flagellin alone or in combination with S. pneumoniae provoked a dramatic increase in Cxcl1, Cxcl2 and Ccl20 mRNA levels as compared to pneumococcal challenge. Flagellin treatment also increased expression of Tnf; although the difference was consistent, it was not statistically significant. Expression of Il6 was increased in animals that were challenged and treated with flagellin but not in those that received flagellin or S. pneumoniae alone suggesting a synergistic effect between flagellin and pneumococcal infection on Il6 expression. mRNA levels of Tgfb1, Il17a, Il17f, Il23 and Il4 genes remained unchanged among all groups compared to mock animals.

To assess if expression of proinflammatory genes correlated with inflammation and cellular infiltration into the airways, we performed the histological analysis of lung tissue obtained 24 h after flagellin-treatment and infection. *S. pneumoniae* induced moderate cellular infiltration restricted to certain bronchioles and some perivascular areas close to these bronchioles. On the contrary flagellin treatment, alone or together with the pneumococci, induced edema, and massive infiltration of cells affecting not only perivascular and peribroncheal regions but also some areas of the surrounding lung parenchyma. Remarkably, at day 7 lungs from mice that received flagellin and pneumococci showed complete resolution of the inflammation with no apparent cellular infiltration or edema. These results suggest that flagellin induces a strong but transient inflammatory response that promotes the clearance of bacteria, without causing permanent alteration of lung morphology or function.

Flagellin-Induced Protection Requires Gr-1 Expressing Cells but is Independent of B and T Lymphocytes:

Neutrophils recruitment into the airways is a landmark of both pneumococcal infection and nasal flagellin treatment and here we showed that flagellin treatment and infection activated expression of genes involved in neutrophil recruitment. Thus, we aimed at comparing the kinetics of neutrophils infiltration in animals challenged with *S. pneumoniae* and either treated or not with flagellin. BAL and lungs were collected at different time points after challenge and stained with an anti-Ly6G antibody. Pneumococcal challenge induced recruitment of PMN in all animals. However, mice treated with flagellin at the time of the challenge showed a more rapid and pronounced infiltration of PMN into the airways as compared with mice challenged with *S. pneumoniae* alone. At 24 h, PMN infiltration peaked whatever the groups, and the difference between groups was maximal. However, by 48 hours the numbers of PMN were no longer significantly different between groups. Thus, co-administration of flagellin with pneumococcus promoted a rapid and transient recruitment of high number of neutrophils into the airways.

Subsequently, we determined whether neutrophils were critical for the flagellin-mediated protection. For this purpose, animals were injected i.p. with a monoclonal antibody specific for granulocyte receptor-1 (Gr-1 or Ly6G/Ly6C) or isotype control antibody 24 h before challenge. Animals that received isotype control and were treated with FliC survived to challenge. In contrast, anti-Gr-I treatment depleted >95% neutrophils from the airways and abrogated flagellin-mediated protection against *S. pneumoniae*. These results showed that Gr-1-expressing cells, likely PMN, are critical effectors of flagellin-induced protection in pneumococcal infection.

As B and T lymphocytes have been involved in the early phase of pneumococcal infection, we evaluated their role in flagellin-induced protection. SCID mice (deficient for antibodies, B and T cells) as well as immunocompetent BALB/c mice were challenged with $2 \times 10^7$ CFU of *S. pneumoniae* or *S. pneumoniae* with flagellin. Lungs and spleen were collected 36 h after infection to determine bacterial counts. Flagellin co-administration promoted clearance of bacteria in the lungs of SCID mice to a similar extent than in BALB/c mice. Both SCID and BALB/c mice also showed lower bacterial counts in the spleen upon flagellin treatment meaning that they were able to control not only local, but also systemic infection. SCID mice recruited similar numbers of PMN into the lungs and alveolar spaces 16 h upon instillation of flagellin when compared to BALB/c mice. In summary, these results show that Gr-1-expressing cells require neither B cells nor T lymphocytes to trigger flagellin-induced protection.

Discussion:

Innate immunity is essential for controlling pneumococcal infection as shown by TLR as well as MyD88 requirement to prevent early colonization of the respiratory tract by *S. pneumoniae* (Albiger, B., Sandgren A., Katsuragi H., Meyer-Hoffert U., Reiter K., Wartha F., Hornef M., Normark S. and Normark B. H. 2005. Myeloid differentiation factor 88-dependent signalling controls bacterial growth during colonization and systemic pneumococcal disease in mice. Cell Microbiol 7:1603-1615; Khan, A. Q., Q. Chen, Z.-Q. Wu, J. C. Paton, and C. M. Snapper. 2005. Both innate immunity and type 1 humoral immunity to *Streptococcus pneumoniae* are mediated by MyD88 but differ in their relative levels of dependence on Toll-Like Receptor 2. Infect. Immun. 73:298-307). Immune response to airway pneumococcal infection is characterized by a great and brisk recruitment of neutrophils into the lungs, and phagocytic killing of pneumococcus by PMN is considered a major defense mechanism. Nevertheless, *S. pneumoniae* can evade host's innate defenses by inhibiting or delaying complement deposition and respiratory burst of phagocytes. Hence, the neutrophil influx is often ineffective in clearing the infection until serotype-specific antibodies are produced and bypass complement deposition inhibition enhancing opsono-phagocytosis. In this study we assessed whether exogenous administration of an agonist of a TLR not naturally engaged by *S. pneumoniae*, namely TLR5 agonist flagellin, could strength innate immunity to control acute respiratory pneumococcal infection. We found that local administration of flagellin promoted survival of mice challenged with a lethal dose of *S. pneumoniae* serotype 1 by enhancing local and systemic bacterial clearance. Flagellin treatment was effective when performed before, during and after infection establishment in the BALB/c, C57BL/6 and NMRI mice.

It has been demonstrated that in vivo administration of flagellin upregulates the expression of proinflammatory cytokines. Here we show that coadministration of flagellin at the time of *S. pneumoniae* challenge also upregulates the expression of the PMN-specific chemokine/activator genes Cxcl1 and Cxcl2 and also Tnf and Ccl20 in the lungs whereas *S. pneumoniae* alone was poorly inducing these genes. In agreement with the chemokine and cytokine expression profile, analysis of lung tissue sections showed a massive infiltration of cells in the peribroncheal and perivascular regions that was more pronounced in the lungs of flagellin-treated animals than in infected non-treated animals. Noteworthy, despite the pronounced inflammatory response induced by flagellin, lung tissue was fully recovered by day 7, while untreated animals died of infection. The analysis of BAL samples suggested that administration of the TLR5 agonist at the time of pneumococcal challenge induced accelerated and more pronounced PMN recruitment. PMN infiltration was transient, peaked at 24 h and regressed to steady state levels at 40 h. Depletion of Gr-1-expressing cells, most likely PMN, abolished the protection demonstrating that these cells are necessary for controlling pneumococcal lung infection. The self-limiting nature of the flagellin-mediated inflammatory response is a very relevant finding since exacerbated inflammation could be associated to failure of lung barrier and function. The molecular mechanisms controlling TLR5 response do not only upregulate pro-inflammatory genes but also trigger response termination. Therefore, flagellin mucosal treatment could be considered as a therapy against pneumococcal pneumonia enhancing neutrophil infiltration and concurrent limitation of inflammation that merits further evaluation in clinical trials.

Besides PMN, several studies have also reported that T and B lymphocytes as well as natural antibodies may play an important role in the early control of pneumococcal pneumonia. It was showed that T lymphocytes accumulate in zones of peribroncheal inflammation at early stages of the immune response and are involved in the defense against pneumococcus since MHC class II-deficient mice lacking CD4+ T cells are more susceptible to infection compared to their wild type counterparts. It was showed that CD19-deficient mice, which have impaired development of B1a cells and natural antibody production, have increased susceptibility to pneumococcal infection. However, the results presented here show that neither T nor B cells are required for flagellin-induced local and systemic clearance of bacteria. Taken together, our results strongly suggest that changing the PMN dynamic results in effective killing of the pneumococci, even in the absence of B and T lymphocytes.

Our results also showed that TLR5 signaling is required for the protection induced by flagellin. In the airways, TLR5 is expressed by alveolar macrophages and epithelial cells, suggesting that these resident cells may be key players in the induction of protective innate defenses against *S. pneumoniae* upon flagellin treatment. In line with this, recent studies suggested that the airway epithelium is the TLR5-activated tissue involved in chemokine production and PMN recruitment in response to flagellated bacteria. On the other hand murine neutrophils express TLR5, thus TLR5 signaling may also directly activate PMN and enhance their *S. pneumoniae* killing capacity. In a similar fashion, it was previously established that heat killed *Haemophilus influenzae* can specifically increase PMN capacity to kill pneumococcus in a Nod1-dependent manner.

Current therapies for prophylaxis and treatment of *S. pneumoniae* infection have limitations in preventing or curing pneumococcal disease, thus new strategies of immune-intervention are still required. Several reports have shown that administration of bacterial lysates and whole heat killed bacteria stimulate protective responses against infection. However, the undefined nature of these preparations is usually a problem when designing drugs for human use. Our results showed that local stimulation with a single and well characterized molecule, specifically flagellin, is sufficient for augmenting lung innate immune defenses and control pneumococcal pneumonia, highlighting the benefits of using Microbe-Associated Molecular Patterns as the basis for developing antimicrobial therapies.

REFERENCES

Throughout this application, various references describe the state of the art to which this invention pertains. The disclosures of these references are hereby incorporated by reference into the present disclosure.

The invention claimed is:

1. A method of treating an acute respiratory tract infection comprising administering to a subject that has an acute respiratory tract infection caused by *Streptococcus pneumonia* a therapeutically effective amount of a TLR5 agonist, wherein the TLR5 agonist consists of a flagellin polypeptide, and wherein said TLR5 agonist is administered topically by intranasal administration or pulmonary administration.

2. The method of claim 1, wherein said flagellin polypeptide is isolated from a bacterium selected from the group consisting of *Escherichia, Enterobacter, Erwinia, Klebsiella, Proteus, Salmonella, Serratia, Shigella, Bacillus, Pseudomonas*, and *Streptomyces*.

3. The method of claim 1, wherein an amino acid sequence of said flagellin polypeptide is selected from the group consisting of SEQ ID NO:1; SEQ ID NO:2; SEQ ID NO:3; an amino acid sequence at least 90% identical to SEQ ID NO: 1, SEQ ID NO:2 or SEQ ID NO:3; an amino acid sequence at least 95% identical to SEQ ID NO: 1, SEQ ID NO:2 or SEQ ID NO:3; an amino acid sequence at least 97% identical to SEQ ID NO: 1, SEQ ID NO:2 or SEQ ID NO:3; an amino acid sequence at least 98% identical to SEQ ID NO: 1, SEQ ID NO:2 or SEQ ID NO:3; and an amino acid sequence at least 99% identical to SEQ ID NO: 1, SEQ ID NO:2, or SEQ ID NO:3.

4. The method of claim 1, wherein said flagellin polypeptide comprises: a) a N-terminal peptide having at least 90% amino acid identity with an amino acid sequence starting from the amino acid residue located at position 1 of SEQ ID NO:3 and ending at any one of the amino acid residues located at positions 99 to 173 of SEQ ID NO:3; and b) a C-terminal peptide having at least 90% amino acid identity with the amino acid sequence starting at any one of the amino acid residues located at positions 401 to 406 of SEQ ID NO:3 and ending at the amino acid residue located at position 494 of SEQ ID NO:3, wherein: the N-terminal peptide is directly linked to the C-terminal peptide, or the N-terminal peptide and the C-terminal peptide are indirectly linked, one to the other, through a spacer chain.

5. The method of claim 4, wherein the N-terminal peptide is selected from the group consisting of amino acid sequence 1-99 of SEQ ID NO:3; amino acid sequence 1-137 of SEQ ID NO:3, amino acid sequence 1-160 of SEQ ID NO:3; and amino acid sequence 1-173 of SEQ ID NO:3.

6. The method of claim 4, wherein said C-terminal peptide is selected from the group consisting of amino acid sequence 401-494 of SEQ ID NO:3 and amino acid sequence 406-494 of SEQ ID NO:3.

7. The method of claim 4, wherein said N-terminal and C-terminal peptides are selected from the group consisting of: amino acid sequence 1-173 of SEQ ID NO:3 and amino acid sequence 401-494 of SEQ ID NO:3, respectively; amino acid sequence 1-160 of SEQ ID NO:3 and amino acid sequence 406-494 of SEQ ID NO:3, respectively; and amino acid sequence 1-137 of SEQ ID NO:3 and amino acid sequence 406-494 of SEQ ID NO:3, respectively.

8. The method of claim 4, wherein the N-terminal peptide and the C-terminal peptide are indirectly linked, one to the other, through an intermediate spacer chain comprising a peptide sequence NH2-Gly-Ala-Ala-Gly-COOH (SEQ ID NO:4).

9. The method of claim 4, wherein the asparagine amino acid residue located at position 488 of SEQ ID NO:3 is replaced by a serine.

10. The method of claim 4, wherein said flagellin polypeptide comprises an additional methionine residue at the N-terminal end.

11. The method of claim 1, wherein said flagellin polypeptide consists of: a) a N-terminal peptide having at least 90% amino acid identity with an amino acid sequence starting from the amino acid residue located at position 1 of SEQ ID NO:3 and ending at any one of the amino acid residues located at positions 99 to 173 of SEQ ID NO:3; and b) a C-terminal peptide having at least 90% amino acid identity with the amino acid sequence starting at any one of the amino acid residues located at positions 401 to 406 of SEQ ID NO:3 and ending at the amino acid residue located at position 494 of SEQ ID NO:3, wherein: the N-terminal peptide is directly linked to the C-terminal peptide or the N-terminal peptide and the C-terminal peptide are indirectly linked, one to the other, through a spacer chain consisting of a peptide sequence NH2-Gly-Ala-Ala-Gly-COOH (SEQ ID NO:4).

12. The method of claim 11, wherein the N-terminal peptide is selected from the group consisting of amino acid sequence 1-99 of SEQ ID NO:3; amino acid sequence 1-137 of SEQ ID NO:3, amino acid sequence 1-160 of SEQ ID NO:3; and amino acid sequence 1-173 of SEQ ID NO:3.

13. The method of claim 11, wherein said C-terminal peptide is selected from the group consisting of amino acid sequence 401-494 of SEQ ID NO:3 and amino acid sequence 406-494 of SEQ ID NO:3.

14. The method of claim 11, wherein said N-terminal and C-terminal peptides are selected from the group consisting of: amino acid sequence 1-173 of SEQ ID NO:3 and amino acid sequence 401-494 of SEQ ID NO:3, respectively; amino acid sequence 1-160 of SEQ ID NO:3 and amino acid sequence 406-494 of SEQ ID NO:3, respectively; and amino acid sequence 1-137 of SEQ ID NO:3 and amino acid sequence 406-494 of SEQ ID NO:3, respectively.

15. The method of claim 1, wherein said flagellin polypeptide consists of: a) a N-terminal peptide having at least 90% amino acid identity with an amino acid sequence starting from the amino acid residue located at position 1 of SEQ ID NO:3 and ending at any one of the amino acid residues located at positions 99 to 173 of SEQ ID NO:3; and b) a C-terminal peptide having at least 90% amino acid identity with the amino acid sequence starting at any one of the amino acid residues located at positions 401 to 406 of SEQ ID NO:3 and ending at the amino acid residue located at position 494 of SEQ ID NO:3, wherein: the N-terminal peptide is directly linked to the C-terminal peptide or the N-terminal peptide and the C-terminal peptide are indirectly linked, one to the other, through a spacer chain consisting of a peptide sequence NH2-Gly-Ala-Ala-Gly-COOH (SEQ ID NO:4), wherein the asparagine amino acid residue located at position 488 of SEQ ID NO:3 is replaced by a serine.

16. The method of claim 1, wherein said flagellin polypeptide consists of: a) a N-terminal peptide having at least 90% amino acid identity with an amino acid sequence starting from the amino acid residue located at position 1 of SEQ ID NO:3 and ending at any one of the amino acid residues located at positions 99 to 173 of SEQ ID NO:3; and b) a C-terminal peptide having at least 90% amino acid identity with the amino acid sequence starting at any one of the amino acid residues located at positions 401 to 406 of SEQ ID NO:3 and ending at the amino acid residue located at position 494 of SEQ ID NO:3, wherein: the N-terminal peptide is directly linked to the C-terminal peptide or the N-terminal peptide and the C-terminal peptide are indirectly linked, one to the other, through a spacer chain consisting of a peptide sequence NH2-Gly-Ala-Ala-Gly-COOH (SEQ ID NO:4), wherein said flagellin polypeptide comprises an additional methionine residue at the N-terminal end.

* * * * *

SEQUENCE LISTING

```
<160> NUMBER OF SEQ ID NOS: 4

<210> SEQ ID NO 1
<211> LENGTH: 585
<212> TYPE: PRT
<213> ORGANISM: Escherichia coli

<400> SEQUENCE: 1

Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Thr
                85                  90                  95

Val Gln Ala Thr Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asp Gly Ser Met
    130                 135                 140

Lys Ile Gln Val Gly Ala Asn Asp Gly Glu Thr Ile Thr Ile Asp Leu
145                 150                 155                 160

Lys Lys Ile Asp Ser Asp Thr Leu Gly Leu Asn Gly Phe Asn Val Asn
                165                 170                 175

Gly Lys Gly Thr Ile Thr Asn Lys Ala Ala Thr Val Ser Asp Leu Thr
            180                 185                 190
```

```
Ser Ala Gly Ala Lys Leu Asn Thr Thr Thr Gly Leu Tyr Asp Leu Lys
        195                 200                 205

Thr Glu Asn Thr Leu Leu Thr Thr Asp Ala Ala Phe Asp Lys Leu Gly
    210                 215                 220

Asn Gly Asp Lys Val Thr Val Gly Gly Val Asp Tyr Thr Tyr Asn Ala
225                 230                 235                 240

Lys Ser Gly Asp Phe Thr Thr Lys Ser Thr Ala Gly Thr Gly Val
                245                 250                 255

Asp Ala Ala Gln Ala Ala Asp Ser Ala Ser Lys Arg Asp Ala Leu
                260                 265                 270

Ala Ala Thr Leu His Ala Asp Val Gly Lys Ser Val Asn Gly Ser Tyr
            275                 280                 285

Thr Thr Lys Asp Gly Thr Val Ser Phe Glu Thr Asp Ser Ala Gly Asn
    290                 295                 300

Ile Thr Ile Gly Gly Ser Gln Ala Tyr Val Asp Asp Ala Gly Asn Leu
305                 310                 315                 320

Thr Thr Asn Asn Ala Gly Ser Ala Ala Lys Ala Asp Met Lys Ala Leu
                325                 330                 335

Leu Lys Ala Ala Ser Glu Gly Ser Asp Gly Ala Ser Leu Thr Phe Asn
                340                 345                 350

Gly Thr Glu Tyr Thr Ile Ala Lys Ala Thr Pro Ala Thr Thr Pro
            355                 360                 365

Val Ala Pro Leu Ile Pro Gly Ile Thr Tyr Gln Ala Thr Val Ser
    370                 375                 380

Lys Asp Val Val Leu Ser Glu Thr Lys Ala Ala Ala Thr Ser Ser
385                 390                 395                 400

Ile Thr Phe Asn Ser Gly Val Leu Ser Lys Thr Ile Gly Phe Thr Ala
                405                 410                 415

Gly Glu Ser Ser Asp Ala Ala Lys Ser Tyr Val Asp Lys Gly Gly
            420                 425                 430

Ile Thr Asn Val Ala Asp Tyr Thr Val Ser Tyr Ser Val Asn Lys Asp
        435                 440                 445

Asn Gly Ser Val Thr Val Ala Gly Tyr Ala Ser Ala Thr Asp Thr Asn
        450                 455                 460

Lys Asp Tyr Ala Pro Ala Ile Gly Thr Ala Val Asn Val Asn Ser Ala
465                 470                 475                 480

Gly Lys Ile Thr Thr Glu Thr Ser Ala Gly Ser Ala Thr Thr Asn
            485                 490                 495

Pro Leu Ala Ala Leu Asp Asp Ala Ile Ser Ser Ile Asp Lys Phe Arg
            500                 505                 510

Ser Ser Leu Gly Ala Ile Gln Asn Arg Leu Asp Ser Ala Val Thr Asn
            515                 520                 525

Leu Asn Asn Thr Thr Thr Asn Leu Ser Glu Ala Gln Ser Arg Ile Gln
    530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
                565                 570                 575

Gln Gln Val Leu Ser Leu Leu Gln Gly
        580                 585

<210> SEQ ID NO 2
<211> LENGTH: 495
```

<212> TYPE: PRT
<213> ORGANISM: Salmonella typhimurium

<400> SEQUENCE: 2

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400
```

Ala Ala Thr Thr Thr Glu Asn Pro Leu Gln Lys Ile Asp Ala Ala Leu
            405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
            435                 440                 445

Ser Ala Arg Ser Arg Ile Glu Asp Ser Asp Tyr Ala Thr Glu Val Ser
            450                 455                 460

Asn Met Ser Arg Ala Gln Ile Leu Gln Ala Gly Thr Ser Val Leu
465                 470                 475                 480

Ala Gln Ala Asn Gln Val Pro Gln Asn Val Leu Ser Leu Leu Arg
            485                 490                 495

<210> SEQ ID NO 3
<211> LENGTH: 494
<212> TYPE: PRT
<213> ORGANISM: Salmonella typhimurium

<400> SEQUENCE: 3

Ala Gln Val Ile Asn Thr Asn Ser Leu Ser Leu Leu Thr Gln Asn Asn
1               5                   10                  15

Leu Asn Lys Ser Gln Ser Ala Leu Gly Thr Ala Ile Glu Arg Leu Ser
            20                  25                  30

Ser Gly Leu Arg Ile Asn Ser Ala Lys Asp Asp Ala Ala Gly Gln Ala
            35                  40                  45

Ile Ala Asn Arg Phe Thr Ala Asn Ile Lys Gly Leu Thr Gln Ala Ser
50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
            85                  90                  95

Gln Ser Ala Asn Ser Thr Asn Ser Gln Ser Asp Leu Asp Ser Ile Gln
            100                 105                 110

Ala Glu Ile Thr Gln Arg Leu Asn Glu Ile Asp Arg Val Ser Gly Gln
            115                 120                 125

Thr Gln Phe Asn Gly Val Lys Val Leu Ala Gln Asp Asn Thr Leu Thr
130                 135                 140

Ile Gln Val Gly Ala Asn Asp Gly Glu Thr Ile Asp Ile Asp Leu Lys
145                 150                 155                 160

Gln Ile Asn Ser Gln Thr Leu Gly Leu Asp Thr Leu Asn Val Gln Gln
            165                 170                 175

Lys Tyr Lys Val Ser Asp Thr Ala Ala Thr Val Thr Gly Tyr Ala Asp
            180                 185                 190

Thr Thr Ile Ala Leu Asp Asn Ser Thr Phe Lys Ala Ser Ala Thr Gly
            195                 200                 205

Leu Gly Gly Thr Asp Gln Lys Ile Asp Gly Asp Leu Lys Phe Asp Asp
            210                 215                 220

Thr Thr Gly Lys Tyr Tyr Ala Lys Val Thr Val Thr Gly Gly Thr Gly
225                 230                 235                 240

Lys Asp Gly Tyr Tyr Glu Val Ser Val Asp Lys Thr Asn Gly Glu Val
            245                 250                 255

Thr Leu Ala Gly Gly Ala Thr Ser Pro Leu Thr Gly Gly Leu Pro Ala
            260                 265                 270

Thr Ala Thr Glu Asp Val Lys Asn Val Gln Val Ala Asn Ala Asp Leu

```
                    275                 280                 285
Thr Glu Ala Lys Ala Ala Leu Thr Ala Ala Gly Val Thr Gly Thr Ala
    290                 295                 300

Ser Val Val Lys Met Ser Tyr Thr Asp Asn Asn Gly Lys Thr Ile Asp
305                 310                 315                 320

Gly Gly Leu Ala Val Lys Val Gly Asp Asp Tyr Tyr Ser Ala Thr Gln
                325                 330                 335

Asn Lys Asp Gly Ser Ile Ser Ile Asn Thr Thr Lys Tyr Thr Ala Asp
            340                 345                 350

Asp Gly Thr Ser Lys Thr Ala Leu Asn Lys Leu Gly Gly Ala Asp Gly
        355                 360                 365

Lys Thr Glu Val Val Ser Ile Gly Gly Lys Thr Tyr Ala Ala Ser Lys
    370                 375                 380

Ala Glu Gly His Asn Phe Lys Ala Gln Pro Asp Leu Ala Glu Ala Ala
385                 390                 395                 400

Ala Thr Thr Thr Glu Asn Pro Leu Gln Lys Ile Asp Ala Ala Leu Ala
                405                 410                 415

Gln Val Asp Thr Leu Arg Ser Asp Leu Gly Ala Val Gln Asn Arg Phe
                420                 425                 430

Asn Ser Ala Ile Thr Asn Leu Gly Asn Thr Val Asn Asn Leu Thr Ser
            435                 440                 445

Ala Arg Ser Arg Ile Glu Asp Ser Asp Tyr Ala Thr Glu Val Ser Asn
        450                 455                 460

Met Ser Arg Ala Gln Ile Leu Gln Gln Ala Gly Thr Ser Val Leu Ala
465                 470                 475                 480

Gln Ala Asn Gln Val Pro Gln Asn Val Leu Ser Leu Leu Arg
                485                 490

<210> SEQ ID NO 4
<211> LENGTH: 4
<212> TYPE: PRT
<213> ORGANISM: Artificial
<220> FEATURE:
<223> OTHER INFORMATION: linker

<400> SEQUENCE: 4

Gly Ala Ala Gly
1
```